United States Patent [19]

Keller, Jr.

[11] 4,452,248

[45] Jun. 5, 1984

[54] BIDIRECTIONAL PACEMAKER

[76] Inventor: J. Walter Keller, Jr., 8600 SW. 54th Ave., Miami, Fla. 33143

[21] Appl. No.: 310,751

[22] Filed: Oct. 13, 1981

[51] Int. Cl.³ .............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 4,091,817 | 5/1978 | Thaler | 128/419 PG |
| 4,248,238 | 2/1981 | Joseph | 128/419 PG |
| 4,284,082 | 8/1981 | Funke et al. | 128/419 PG |
| 4,312,355 | 1/1982 | Funke | 128/419 PG |

OTHER PUBLICATIONS

"Complete Abolition of the Reentrant Supraventricular Tachycardia Zone Using a New Modality of Cardiac Pacing with Simultaneous Atrioventricular Stimulation"; Jan. 1980, The American Journal of Cardiology, vol. 45, pp. 72-78.

*Primary Examiner*—William E. Kamm

*Attorney, Agent, or Firm*—Oblon, Fisher, Spivak, McClelland & Maier

[57] ABSTRACT

A dual chamber cardiac stimulator provides sequential escape stimuli to the heart for bradycardia by synchronous following of normal sinus rhythm with prosthetic redundant AV coupling pre-empting or substituting for long or blocked physiologic AV delays. The automatic provision for prosthetic conduction of cardiac action in both antero and retrograde directions with pre-emption of pathologic delays prevents the initiation of reentry supraventricular tachyarrhythmias as well as the traditional disrhythms of pacing. Access to both chambers permits automatic injection of simple stimulus programs in either chamber upon the detection of a disrhythm, with immediate interruption by the first normal cardiac event. The pacer responds to arrhythmia provoking events by controlling the conduction time from atrium to ventricle and from ventricle to atrium to maintain cardiac stability and prevent pathological pathways from contributing to satisfy the criteria of reentry tachycardia.

13 Claims, 11 Drawing Figures

BIDIRECTIONAL PACEMAKER

BACKGROUND OF THE INVENTION

1. Field of the Invention

The present invention relates to cardiac pacemakers which involve cardiac stimulation in order to provide a clinically and therapeutically accepted method for correcting heart block, sick sinus node syndrome and specific other arrhythmias.

2. Description of the Prior Art

The parts of heart normally beat in an orderly sequence beginning with the contraction of the atria (atrial systole) and followed by contraction of the ventricles. During the diastole all four chambers of the heart are relaxed. The specialized structures that form the cardiac conduction, including the sino-atrial node (SA node), the atrioventricular node (AV node) the bundle of HIS followed by right and left branches and the Purkinje system, discharge at a more rapid rate than the cardiac muscle itself. The SA node normally discharges most rapidly with the depolarization spreading from it to other regions before they discharge spontaneously. Thus it can be seen that the SA node is the normal inherent cardiac pacemaker with its rate of discharge determining the rate at which the heart beats. The impulses which are generated in the sinus (SA) node pass through the atrial muscle to the AV node on its way to the ventricular muscle.

In the normal human heart, each beat originates in the sinus node with the heart beating about 70 times per minute at rest. The rate is slowed (bradycardia) during sleep and accelerated (tachycardia) by exercise, fever and many other stimuli. Abnormal variations in the heart rate are called sinus arrhythmia. A portion of the AV node sometimes discharges independently and if this occurs once, the result is a beat which occurs before the expected next normal beat and transiently interrupts the cardiac rythm. This is called either an atrial, nodal or ventricular extrasystole or premature beat. If this occurs repetitively at a rate more rapid than that of the sinus node it produces a rapid regular tachycardia. While occasional atrial extrasystoles occur from time to time in most normal elderly humans and have no clinical significance, the repetitive discharge causing atrial tachycardia and flutter resulting in ventricular rates which may indicate that the ventricular rate may be so high that diastole is too short for adequate filling of the ventricules with blood between contractions. This means that the cardiac output is reduced and symptoms of heart failure may appear.

One of the specific treatments for correcting heart block, sick sinus node syndrome and specific other arrhythmias involves "physiological stimulation" of both sets of chambers of the heart. Studies have been conducted of the so-called sequential stimulation over a wide range of stimulation parameters in connection with a study of the hemodynamic properties of the heart, as reported in an article by Samet et al, entitled "Hemodynamic Sequelae of atrial, Ventricular and Sequential Atrial Ventricular Pacing in Cardiac Patients", *American Heart Journal*, Vol. 72, pages 725-729, December, 1966.

Earlier than that, P-wave synchronous coupling of both chambers was found to produce substantially better antiarrhythmic properties than simple stimulation of the ventricles. As described by Nathan et al in an article entitiled "An Implantable Synchronous Pacemaker for the Long Term Correction of Complete Heart Block", *American Journal of Cardiology*, Vol. 11, page 362, 1963. Bradycardia have been treated with fixed rate ventricular pacing which competed with, or was out of synchronism with, the true sinus rate.

Implantable versions of AV-sequential pacemakers, as they are disclosed in U.S. Pat. No. 3,747,604 and which are based on the work reported in the above-cited article by Samet et al, provide atrial escape stimuli before ventricular escape stimuli so that the protection against arrhythmias is augmented particularly in the bradycardia modes. In this connection, the term "escape stimuli" is intended to mean that the artificial cardiac pacemaker emits a stimulation pulse unless a corresponding signal appears from the heart itself within a given interval.

Studies with an implantable Multimode A-V Pacemaker for Reciprocating Atrioventricular Tachycardias, PACE, Vol. 3, May, 1980, indicate ways in which arrhythmias can be initiated, eliminated and suppressed by suitable stimulation of one of the two chambers of the heart, even if in some patients coupling is effected in the reverse direction.

The literature on cardiac arrhythmias is replete with diagrams and listings of criteria for the "Reentry Arrhythmias" of the dominant type where two stimulation pathways must exist to maintain the arrhythmia. A reentry tachycardia is a fast heat rate caused by reentry path way providing a new cardiac cycle of activity from the previous activity. In a normal heart beat, as discussed above, the sequence of cardiac activity begins at the sinus node, proceeds via the AV node and into the right and left ventricular chambers. The electrical activity produces an atrial contraction followed by delayed ventricular contraction. The depolarization activity originating at the pacemaker cells of the sinus node is extinguished when all of the ventricular cells have depolarized. The cells cannot support further activity until they are repolarized and the new activity is initiated.

During the period when all of the cells in a group are depolarized that area of the heart is said to be in absolute refractory. When part of the cells in a group are repolarized the area is said to be in relative refractory. In a totally non-refractory area it is generally possible for activation to propagation in either direction. However, in an area of relative refractory the direction of propagation favors the area with the greater density of repolarized cells. As will be discussed later, this is one explanation for the direction of propagation tending to go in only one of two possible directions in the pathway. Another possibility is when one path is fully recovered in front of new activity while the other path has slowly recovering cells to obstruct propagation of new activity. When the activity traverses the first path and echos back along the second path it encounters fully recovered cells making continued propagation possible.

When there is only one pathway from the atria to the ventricle there can be no reentry and no restarting of cardiac activity. Thus it can be seen that one of the primary requirements for reentry tachycardia is two conducting pathways that form a closed loop where activity can propagate around the loop sustaining itself. This closed loop acts as a pacemaker where each transit around the loop provides new excitation to chambers of the heart that are linked by conductive paths to the loop. This requirement for a bifurcated pathway from the atrium to the ventricle is shown in the FIG. 1.

If the propagation time around the loop is shorter than the refractory period of cells everywhere in the loop the propagation will be stopped when the activity collides with the refractory cells. Therefore a second criteria for reentry tachycardia is that the conduction time in the loop must be relatively long compared to the refractory times throughout the loop so that at least somewhere in one of the branches there must be a relatively slow propagation of activity.

A third criteria for the reentry tachycardia to take place is that upon entry or beginning of activity, one of the conducting pathways must at least temporarily block or be refractory to excitation. This is evident from the fact that when activity enters the loop from one of the chambers and conduction takes place in both directions the activity will be extinguished when they collide on the other side of the loop. However, if upon entering the loop it propagates in only one of the two directions it will not be extinguished and it is now free to continue to conduct around the loop forming the undesirable reentry tachycardia. The FIG. 1 illustrates a path formed by a closed loop which includes no tissue from either the atria or the ventricals. There are conducting links from the closed loop to each of the two heart chambers. It is assumed in artificial electrical pacing that there is no direct access to the loop other than the access provided by the links to the heart chambers where electrodes can be located. The properties of these links determine the accessability of the loop for an arrhythmia breaking event.

A normal sinus beat is illustrated by the FIG. 2 with the darkened areas indicating a depolarization region which begins at the sinus node in the atrium and progresses down both branches of the loop, although slightly slower in the right branch. FIG. 2c illustrates the position of the activity or depolarization which occurs when the left branch or the faster branch is depolarized to the ventricle area. It should be noted that as the activity reaches the ventricle it proceeds to go up the right or slower path where it collides with the activity coming down the slower or right branch. The FIG. 2d illustrates all of the area being depolarized and the FIG. 2e indicates a recovery of the atrium with a relative refractory part shown in the lower right side of the atrium. The link from the atria to the two paths is fully recovered and repolarization of the tissues in the right and left branches progressing a shown. the dots represent pockets of late recovering cells which can be left after all other cells surrounding the pocket have recovered.

FIG. 3 indicates an example of the operation of a premature atrial stimulation systole. The activity spreads from the atrial stimulus $S_a$ before the top link of the AV path is fully recovered, as is illustrated in FIG. 3a. From that point the stimulation activity is seen to reach the top of the loop where the two paths bifurcate, in FIG. 3b at which point in time the tissue is in relative refractory. The density of the repolarized cells to the left is higher and conductivity is favored in that direction and blocked to the right. Another possibility is that all the cells at the top of both paths could be fully recovered and the approaching activity could go in both directions with recovering cells just ahead of the activity. At that point a pocket of late recovering cells in the right path could block conduction which continues unabated in the left branch. The FIG. 3c illustrates that repolarization from the previous beat proceeds in both paths while propagation of the new early beat continues only in the left path. The FIGS. 3d and 3e illustrates the new activity reaching the bottom junction of the paths and finding non refractory cells in both directions permitting propagation both to the ventricles and back toward the atria. FIG. 3f illustrates the activation reaching the top along the fully recovered right branch where it finds the first part of the left branch sufficiently repolarized to support propagation. The final step in the reentry process is accomplished as shown in FIG. 3g which shows the looping process which will be sustained as long as the speed of propagation is slower than the recovery time (refractory) of the cells of the loop.

Thus it can be seen that the three criteria for reentry tachycardia are (1) Two pathways, (2) Relatively slow conduction somewhere in the loop and, (3) Unidirectional conduction in one of the paths. The activity continues to propagate around the loop until cardiac parameters change enough to fail to satisfy the three criteria. Each time the activation passes the top or the bottom of the loop it branches out to stimulate the respective chamber except when the link or the chamber is refractory.

The literature on cardiac arrhythmia is replete with diagrams in listing of criteria for the "reentry arrhythmia" of the dominate type where two stimulation pathways must exists to maintain the arrhythmia. It is shown that delay periods of the loop must be relatively long to meet the requirement for sustained reentry. All prior art attempts to terminate tachyarrhythmias by stimulation have the drawback that the success "in the various methods per se" is not yet satisfactory.

SUMMARY OF THE INVENTION

It is an object of the present invention to provide a cardiac pacemaker of the above described type which offers improved possibilities for preventing and terminating reentry arrhythmias.

The above and other objects according to the invention are achieved by providing a cardiac pacemaker constructed for preventing and terminating tachycardias and including an atrial electrode implanted in or near a patients' atrial wall for supplying atrial stimulation pulses thereto but inhibiting (or synchronizing) stimulation in response to each atrial contraction. There is also provided a ventricular electrode implanted in, or near the ventricular wall for supplying ventricular stimulation pulses thereto. Other features include a means by which the pacemaker supplies control paths for causing one electrode to produce a stimulation pulse at a given time after the occurrence of a signal on the other electrode and a first time delay unit connected to be actuated by signals derived from the heart behavior for supplying a stimulation pulse to the ventricular electrode at a specific time after the occurrence of a signal on the atrial electrode. This serves as a parallel path for the physiological atrial-ventricular transfer time. A second time delay unit is provided which is actuated by signals derived from the heart behavior for supplying a stimulating pulse to the atrial electrode at a time after the occurrence of a signal on the ventricular electrode. These dual pacer pathways are intended to substitute for or pre-empt any physiological delay path that might exist.

The present invention is based on a realization that a plurality of control pathways or patterns must be available in order to master the normal and abnormal physiological delays which predispose the heart to beat at undesirably fast rates.

Prior to the present invention, none of the efforts concerned with prosthetic stimulation treatments considered the necessity of a sequence recognition of cardiac activation and response in both directions within a single stimulation concept. Spurrel et al, "Pacing Techniques in the Management of Supraventricular Tachycardias", *J Electrocariol* 1976; 9: 89–96 found satisfactory results in some patients using very short pre-emptive AV delays and Coumel et al, "Tachycardie permanente par rhytme reciproque. I. Preuves du diagnostic par stimulation auricularire. II. Traitement par l'implantation intracorporelle d'un stinulateur cardique avec entrainement simultane de l'oreillette et du ventricule", *Arch Mal Coeur* 1967; 60: 1830–64 obtained satisfactory results in the opposite direction in particular patients by the use of simultaneous pacing. But as yet no one has recognized the advantage of an automatic recognition of specific patient's needs by the recognition of sequence and responding automatically and immediately to provide the correct action.

The present invention discovered the needs and the means for its recognition by responding in the required direction automatically to thereby supply corrective measures for both classes of patients in the same unit while still being capable of providing optimum hemodynamic pacing to each class during periods of relatively normal rhythm. One of the significant advantages of the present invention is that the total number of patients whose needs can be meet is greater than could be expected merely by the sum of those for whom each of the two measures is appropriate since the two therapeutic measures supplement one another and are able to produce a termination of a tachycardia even in those cases where one of the two measures alone would not have accomplished the desired result. Thus these two measures which rely on the use of both directions within a single stimulation concept provide an increase in the mumber of arrhythmia patients responding to stimulation therapy beyond those which are able to be helped by the prior art concept.

The criteria stated in the cited prior art shows a relationship of the propagation time through natural and additional paths to the cardiac interval and a relationship of the refractive period to the cardiac interval. These functional relationships are the major factors which permit initiation or enhancement of a tachycardia. It is evident from the cited literature that the propagation time may also be extended or the refractory period shortened if the cardiac cycles are shortened. If early stimulation somewhere in the loop formed by two paths linking atria to ventricle happens to be refractory in one direction and, once it continues on the other path, proceeds around the loop at a relatively slow rate, it will not find all of the tissue to be refractory upon further propagation. This is the basic mechanism of reentry arrhythmia as discussed above. The reentry into the loop can be interrupted by increasing the refractory period or by decreasing the propagation delay somewhere in the loop. In this connection, it is a significant desirable property of the additional parallel path according to the present invention that the respective periods are shortened within the cycle interval, or at least not changed so that the above-discussed physiological changes can be accounted for.

BRIEF DESCRIPTION OF THE DRAWINGS

FIG. 6a is a diagram of EKG signals used to explain the operation of the invention.

FIGS. 6b–6g are time diagrams showing the pulse behavior of various groups of pacemaker components with respect to the EKG signals shown in FIG. 6a.

DETAILED DESCRIPTION OF THE PREFERRED EMBODIMENT

Figure 2:
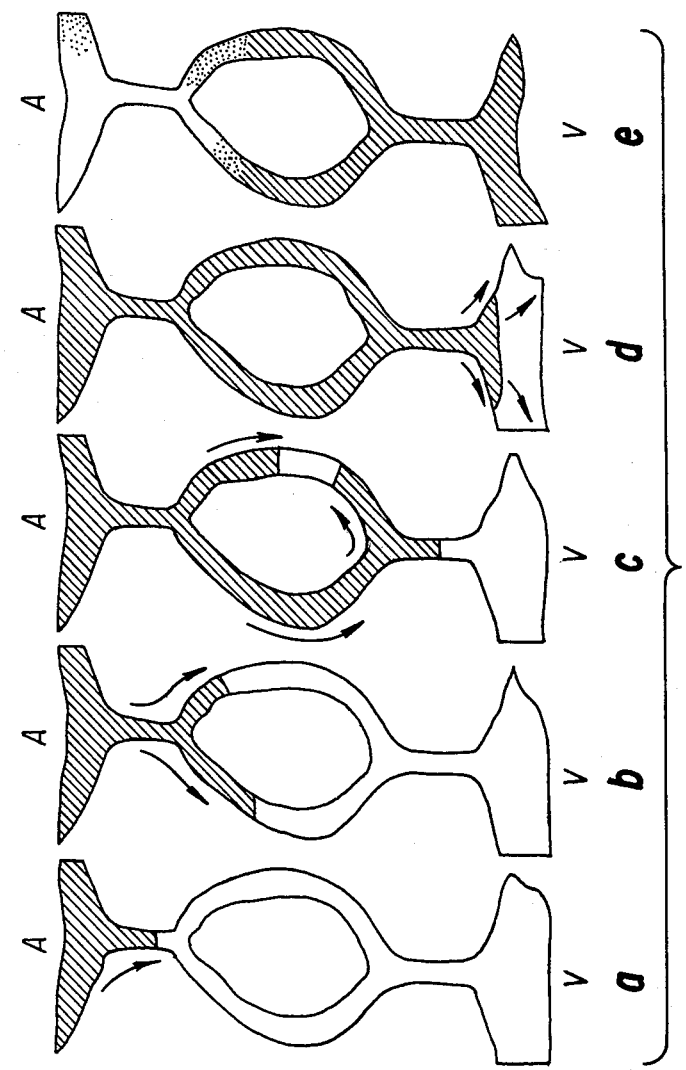
FIG. 2 shows the normal progression of cardiac activity in a bifurcated pathway.
Figure 1:
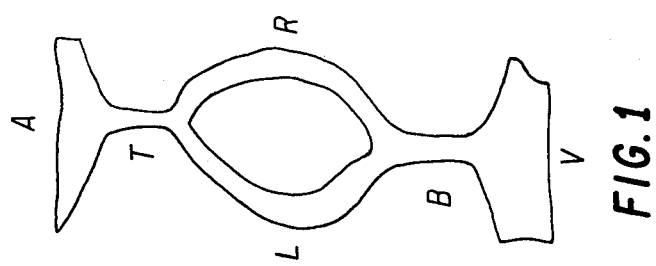
FIG. 1 shows a bifurcated pathway from atria to ventricle.
Figure 3:
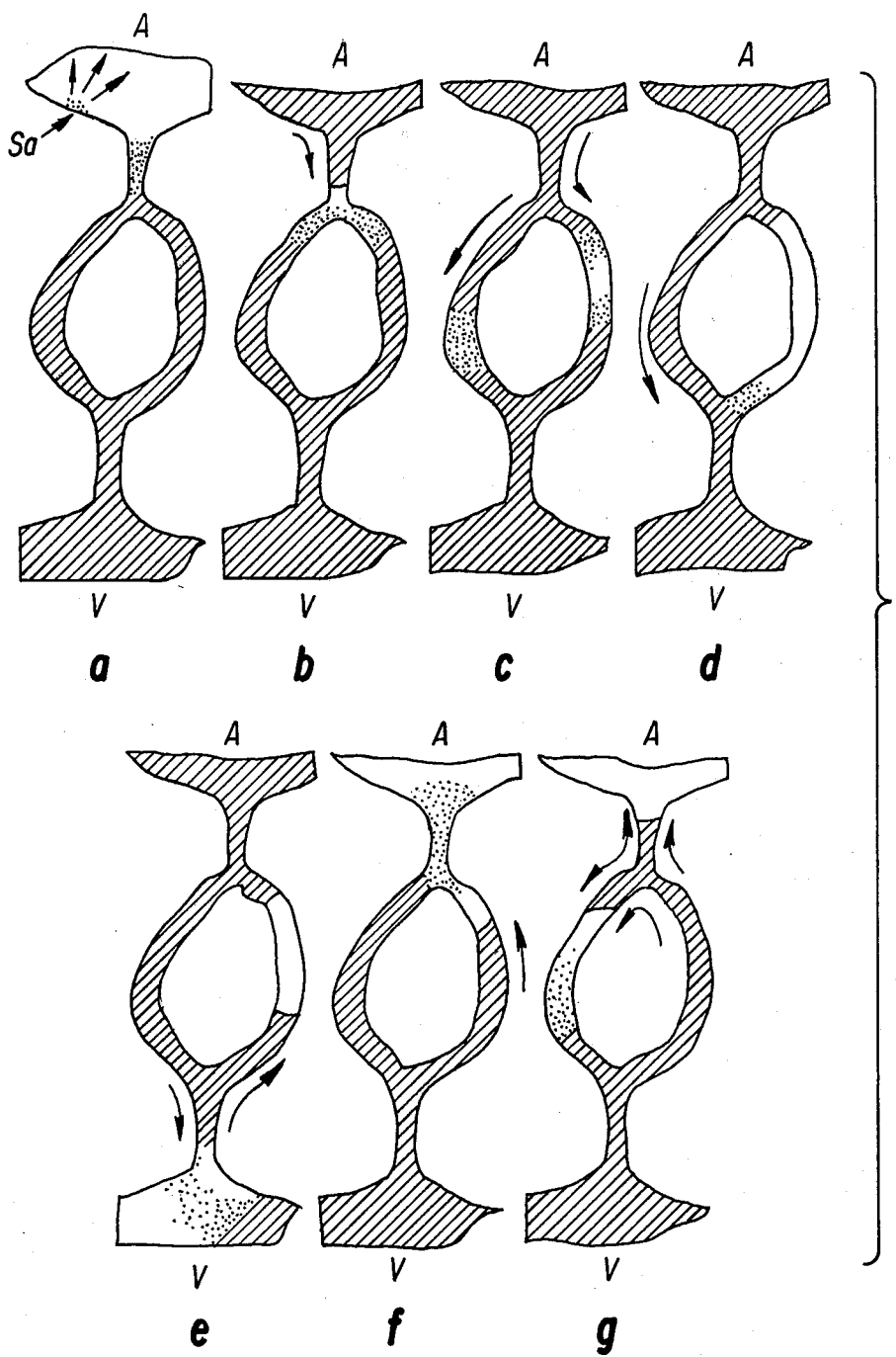
FIG. 3 shows a premature atrial escape originating before the heart has fully recovered from previous activity.
Figure 4:
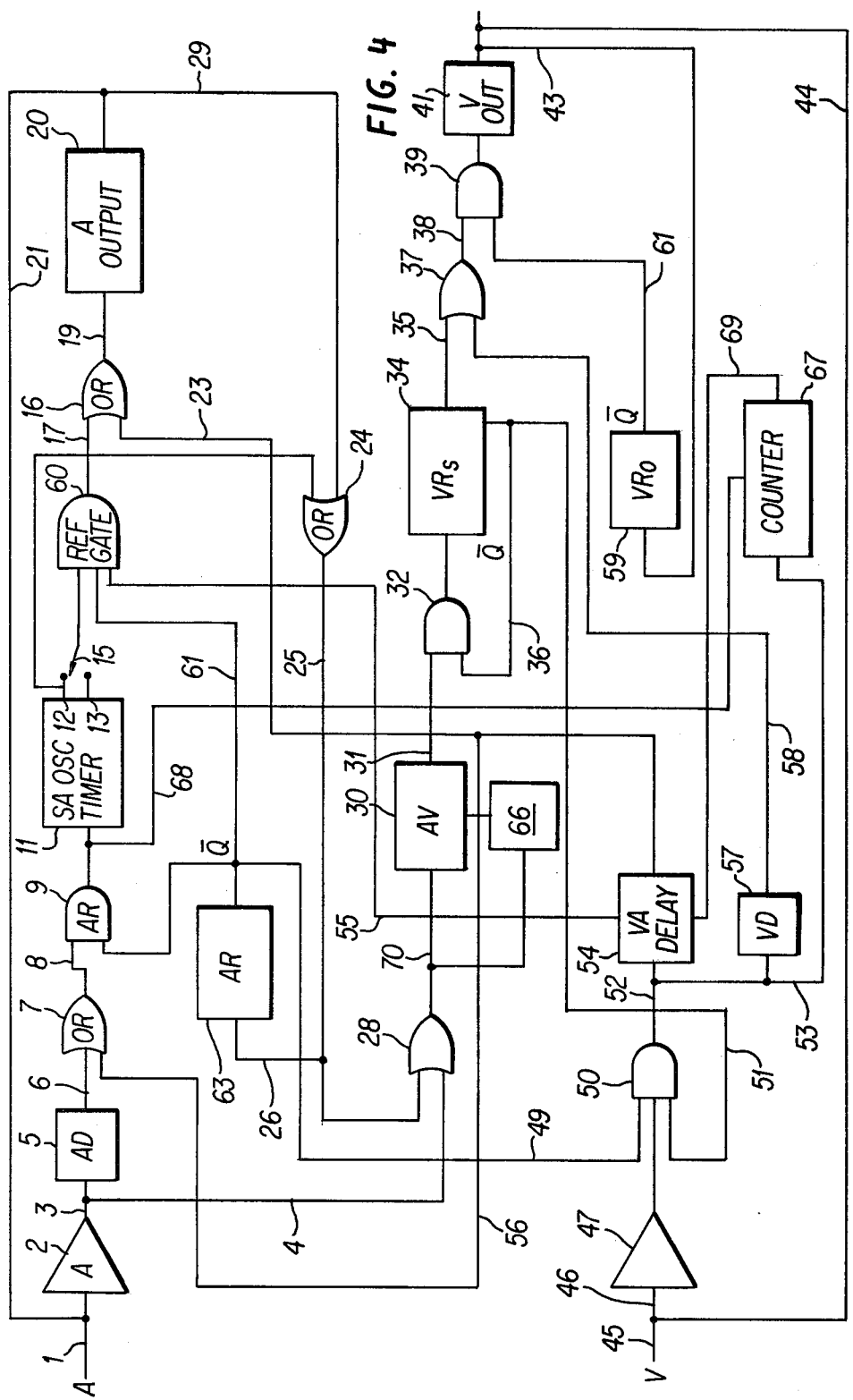
FIG. 4 is a block diagram a pacemaker according to the preferred embodiment of the invention which serves to generate stimulation pulses and to receive and process intracardial signals.

The pacemaker shown in FIG. 4 has a terminal A connected to an electrode 1 placed in, on or near a cardiac atrium. The signal detected by the atrial electrode travels to a frequency selective preamplifier, phase splitter and threshold detecting system indicated at 2. This system detects these signals and amplifies them until that are adequate for actuating subsequential functional stages. The amplifier system 3 is followed by a delay member 5 which produces a signal delay of a few milliseconds. This delay is an important innovation particularly in unipolar pacing systems which assures that the detected signal is not from the ventricle. This provides and allows for a more reliable logical decision evaluating cardiac sequence. The delay is bypassed by line 4 in order to establish a proper timing relationship with cardiac events which follow.

The output of the delay member 5 is followed by an OR gate 7 whose output is fed to an AND gate 9 (AR) which provides a refractory block function for the atrial signal. If the detected input signal by the atrial electrode is beyond the atrial refractory period of the previous cycle it proceeds to reset the sinoatrio escape timer (oscillator) 11. This atrial escape timer 11 provides the cycle time of the pacer and it is possible by switches or remote programming for a physcan to choose to have a synchronous signal output 12 or an output that is only available when the timer runs its full course as indicated by 13. This choice of function is provided through a switch 15. Any escape pulse or synchronous pulse from timer 11 is fed through another refractory AND gate 60 and then through an OR gate 16 in order to trigger an atrial output stimulus from the output pulse control 20 which applies a stimulating pulse to the atria by means of line 21.

The atrial signals or stimuli are also applied to the AV delay function 30 through OR gates 24 and 28. The delay function is initiated by the first of the following three events; (a) a properly timed atrial systole (through the gate 28 via line 4), (b) a pacemaker escape signal from SA OSC11 (through the OR gate 24) and (c) an aberrantly sequenced properly timed ventricular systole that triggers A OUTPUT via VA DELAY 54 through line 23 through OR gate 16 through A OUTPUT 20 and OR gate 24. The earliest of the three above described signals also function to trigger an atrial refractory function 63 which provides, by means of its inverse output, the blocking of the two refractory gates 9 and 60 which in turn block all pacemaker atrial stimulation or recycling until adequate recovery time from the previous cardiac cycle has passed.

The following sequence of activities indicates the operation of the circuit to provide the above-mentioned reaction to a detected atrial event. If the event under question is a spontaneous atrial or sinus escape, the detected signal by amplifier 2 outputs via line 4 an initiation of the AV delay 30. At this point however, the atrial refractory, AR 63, is not yet started in order to assure that the signal is truly of atrial origin. Thus during this period of time produced by the delay AD 5, a ventricular event then has time to be detected and passed by gate 50. Meanwhile, the atrial detected signal proceeds through the delay AD 5, OR 7, AR 9 resetting the SA TIMER 11, which through OR gate 24 triggers the atrial refractory, AR 63. If during this short time no ventricular event has been detected the atrial signal is identified as legitimate and the system proceeds to act as though a proper sequence exists and recycling of the timer with the issuance of a delayed ventricular stimulus takes place. Atrial refractory 63, after the period of time provided by AD 5, produces a "LO" on line 49 causing gate 50 to block any ventricular detected events for the duration of the atrial refractory.

At the end of the AV delay function the signal, if properly non-refractory, traverses the refractory gate function of AND gate 32. This in turn triggers the ventricular sensing refractory delay 34 whose output serves to block the signals at gate 32 via the line 36. The positive output of the sensing refractory circuit proceeds through the OR gate 37 and another refractory function gate 39 to produce a ventricular output from pulse shaping function 41.

The ventricular output is applied via line 44 to the ventricle by means of the ventricular electrode 45. The ventricular output from the pulse shaping function 41 also triggers a ventricular output refractory function 59 which acts through line 61 to the gate 39 in order to limit the rate of pacemaker ventricular stimuli.

One of the main objects of the present invention is to provide prosthetic conduction paths in both the AV and the VA direction. One means for providing this feature is through the detection of ventricular activity and an adequate response. Amplifier 47 serves the function for the ventricles in the same manner that amplifier 2 does for the atrium. A detected ventricular signal proceeds to the refractory gate (AND gate 50). This gate provides the following criteria of acceptance of a ventricular signal: (a) The atria has not already started systole, (b) The ventricular system is no longer in a sensing refractory time. Once these criteria have been satisfied, the system recognizes aberrant sequences and gate 50 outputs in two directions. The primary direction is toward the VA delay 54. At the end of the VA delay 54 an output triggers an atrial output via OR gate 16. Another output of the VA delay 54 provides a refractory (blocking) signal to gate 60 to have the system ignore all atrial system activity during the VA delay function.

If the detected atrial event is a ventricular signal which is detected by amplifier 47, before the expiration of delay AD 5, then the VA delay 54 is triggered. This delay triggers an atrial output via line 23 and also triggers the resetting of a timer 11 via line 56. The next step is the triggering of the delay VD 57 by the output of gate 50 which pre-empts the AV delay 30 to produce a ventricular output with the VD delay rather than the AV delay. If the signal has been a true ventricular systole the ventricular stimulus falls during the ventricular systole refractory. If, on the other hand, the signal is interference, then the atrial and ventricular sequential antiarrhythmic pair is produced rather than a single ventricular stimulus, no stimulus, or a reversion stimulus as was exemplified in the prior art. Finally the third step is an output from 50 providing a clock pulse via line 53 to the PVC counter 67. Subsequently, any true atrial or sinus escape resets counter 67 via line 68. Thus it can be seen that the counter 67 counts ventricular extra systoles and provides an incrementing signal on line 69 to the VA delay 54. The scanning cycle may typically be set to a count of 8. Here, it can also be seen that the AR should be triggered slightly ahead of the counter 67 for ventricular events so that the signals on line 56 do not produce counter reset, but signals via lines 3 and 6 do produce the reset as discussed above.

Because of the knowledge that legimate ventricular events cannot occur very close together, it becomes obvious that no event within the ventricular sensing refractory can be considered truly ventricular. Likewise, when the criteria of atrial recognition, namely, an elaspe of time equal to AD 5 after atrial detection, is satisfied there is no acceptance of ventricular signals. This is provided, as discussed above, by the atrial refractory circuit, AR 63 providing a signal via line 49 to gate 50 which blocks the detection of ventricular events.

The above counter 67 and its output is used to detect if ventricular systoles are consective and provides via the prosthesis an incrementing of the VA conduction time. This provides an automatic responsiveness to the system to detect ventricular extra systoles which are consecutive and therefore dangerous to the condition of the heart as it is very likely that they are the forerunner of a reentry tachycardia or that they are actually a reentry tachycardia in progress.

The system response to a non-refractory aberrant sequence ventricular systole is to provide a controlled delay or atrial stimulus to pre-empt any undesirable pathological pathway to the atrium and defeating the heart in setting up the criteria necessary for a paroxsym of reentry supraventricular tachycardia.

An early cardiac event either from the atria or the ventricle can effect cardiac parameters in order to promote the reentry phenomenon. It is therefore desirable in some patients that the conduction time be changed substantially to help prevent the potential conduction time relative to refractory time relations that satisfy the reentry criteria. With function 66, the AV delay 30 can be automatically changed as a function of degree of prematurity of the atrial beats. Cited literature indicated that the shortening of AV delay was desirable, but technology does not limit the facility to a shortening if subsequent knowledge indicates otherwise. By this device it is detected if a premature atrial event occurs that can shorten the refractory time of connective paths and if this is indeed the case automatic shortening of the prosthetic delay can further contribute to the protection provided.

Typically, a cardiac pacer prothesis might have the following temporal parameters dictated by hemodynamic considerations:
1. AV delay 150 milliseconds.
2. Atrial refractory 250 ms.
3. Ventricular sensing refractory 300 ms.
4. Ventricular output refractory 400 ms.
5. VA delay time, 0 ms.
6. Atrial delay time, 10 ms.

However, the proper parameters to suppress arrhythmias will surely differ from patient to patient. This variation indicates the utility, desirability and practical necessity of remote programmability of a commerically acceptable pacemaker for this broad service. The pacemaker technology has developed in the past 13 years so that it is very versatile and an effective programmable pacer is well within the skill of the art.

Figure 5:
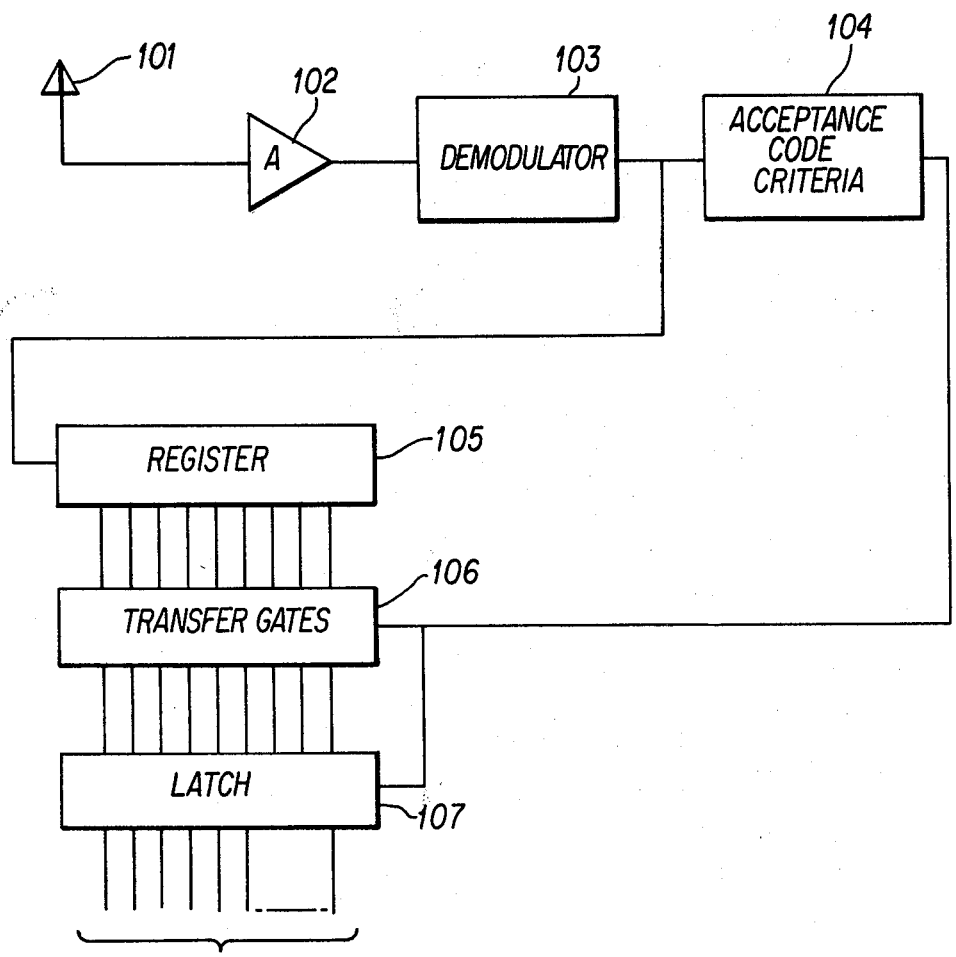
FIG. 5 is a functional block diagram of a programming means for the system of FIG. 4.

The FIG. 5 serves as an indication of the possibilities available from the system disclosed in the FIG. 4. In FIG. 5 the antennae 101 represents a detector of electromagnetic, magnetic, optic, sonic or other carrier utilized for information transfer across a distance. The amplifier 102 amplifies the detected signal to useable levels and the demodulator 103 demodulates the incoming modulated carrier signal. In order to ensure that false signals are not accepted, the signal being encoded is tested for proper coding in function 104. As the demodulator 103 extracts the signal it loads the memory register 105 with the incoming intelligence. If the signal satisfies the acceptance code criteria the output of 104 directs that the information from 105 be transferred by the transferred gate 106 to a latched receptical at 107.

The contents of latch 107 is a code with an output line for each information bit that directs the respective functions of FIG. 4 to assume the program mode and values that are directed. While not all pacemaker parameters and modes should be programmable, modern technology provides an enormous number of options. The limiting factor to the range available is the knowledge and skill available in the medical profession. If too much information is provided the device efficacy will be hindered rather than facilated, the following is a partial list of modes and parameters that could conceivably be used and programmed:
1. Pacemaker output parameters;
2. Pacemaker input parameters;
3. All timing functions, such as delays, refractory periods;
4. Escape rate;
5. Incrementing ratios;
6. Prematurity criteria;
7. Noise mode;
8. Inhibited or synchronous mode of both chambers;
9. Diagnostic mode;
10. Telemetry mode and stored information for telemetry.

Only experience will provide the necessary knowledge to develop the optimum parameters and settings. However, there are many variations of the above characteristics and functions that will be obvious to one skilled in the art. The following is a listing including many such variations:
1. Any spontaneous cardiac activity can provoke either an inhibited pacemaker output or a trigger output. Thus, either portion of the pacemaker could resemble either the so called demand pacer or the so called synchronous pacemakers of the past.
2. One of the sections could be of the demand type while the other section could be of the synchronous type.
3. Technology could easily be provided to obviate or counteract the slaved ventricular response when there is a pre-empting cardiac action. This would provide an inhibited output to the second chamber when there is not need for such output.
4. Instead of the interference characteristics already listed it is possible to provide reversion modes based upon the type of signal sensed. For example, for simultaneous signals encountered on both electrodes at rates above a specified rate the system could provide a fixed or varying sequential rate for satisfactory cardiac action in the presence of the interference. Rapid signals on only the atrial electrode could be made to reproduce refractory limited synchronous sequential stimuli. Rapid signals on only the ventricular electrode could provoke either of the two above characteristics at the option of the physician. The amount of delay VD 57 provides the alternate pacemaker interference characteristics. For example, if the delay is set for about 50 to 100 milliseconds and the atrial synchronous option system is employed the pacemaker response will always be a properly sequenced A followed by a V stimulus, or, in the case of a continuous consecutive PVC's or interference a close coupling alternating over the counter 67 cycle from leading to trailing phase of the A relative to the V stimuli. This relationship in the presence of PVC's offers a very desirable antiarrhythmic action, and in the presence of interference provides suitable hemodynamic and superior electrophysiologic response.
5. To one skilled in the art it is evident that it can be possible to detect both ventricular and atrial activity from a single atrial electrode or unipole. For example, almost anywhere in, on, or near the atrial myocardium a unipolar electrode senses both the atrial and ventricular depolarization. Thus, a pacemaker can be made to respond to either or both cardiac chambers having only one amplifier means. Indeed, it is possible to provide sensing means of both chamber employing a single differential or summing amplifier.

By this method an atrial trigger ventricular slaved pacer could provide assured dual chamber stimuli regardless of the chamber sequence. This means that there will be a retrograde pre-empting as well as an anterograde pre-empting of any possible cardiac pathways providing the basic properties of the present invention. Additionally, it must be pointed out that the fact that a ventricular slaved stimulus in the above pacemaker falls in the ST segment of a spontaneous ventricular systole and is of almost no consequence as demonstrated by this response in the previous so called P-Synchronous pacers used for nearly 20 years.

Furthermore, to one skilled in the art, it is evident that a system of this type which deals with very complex cardiac arrhythmias will be greatly enhanced by including diagnostic means. It will further enhance the system to have means for communicating with the pacemaker for determining its actual detailed program, including its real time response to the exsisting rhythm. Also, for diagnostic purposes there will be a benefit derived from the ability to provoke programmed extra systoles without additional encumbering patient equipment.

A further benefit of the present invention may be used to provide a memory storage in the pacemaker itself for storing specific events or combinations of events for later interrogation by the physician in order to evaluate the specific pacemaker program and or drug regimen, or any exercise program or experience encountered by the patient.

The atrial delay provided in this dual system has a two fold benefit. First, it makes sequence recognition in a unipolar electrode system relatively easy. The other benefit is derived from the fact that in an atrial synchronous mode of dual chamber pacing the synchronous stimulus artifact on the EKG occurs in such a manner that it is delayed just enough to indentify the first portions of the P wave. This is a substantial aid in proper and easy reading of the EKG. The historical advantage of synchronous or triggered responses is that it provides protection against all forms of interference and its override feature is particularly attractive in this kind of arrhythmia directed pacer.

The operation of the above described pacemaker portion will now be described with reference to FIGS. 6a–6g.

FIG. 6a shows the curves of an EKG signal; in FIGS. 6a–6c, the pulses $S_a$ represent stimulation pulses in the atrial and pulses $S_V$ represent stimulation pulses in the ventricles. The signal pattern shown in FIGS. 6b and 6c are the outputs from the atria pulse control 20 and the ventricular pulse control 41, respectively. FIG. 6d shows a signal AV constituted the output from delay member 30 and containing pulses whose duration corresponds to the atrial-ventricular transfer period. Pulses corresponding to the atrial refractory period and the output from the member 63 are shown in FIG. 6e while FIGS. 6f and 6g depict the output of members 34 and 59 respectively, having pulses whose durations correspond to the ventricular refractory periods $VR_s$ and $VR_o$, respectively. It can be seen that the total refractory period for the input signals (sensing) for the ventrical is composed of the sum of the AV delay (minus the AD delay) and the refractory period $VR_s$ of member 34.

Figure 6:
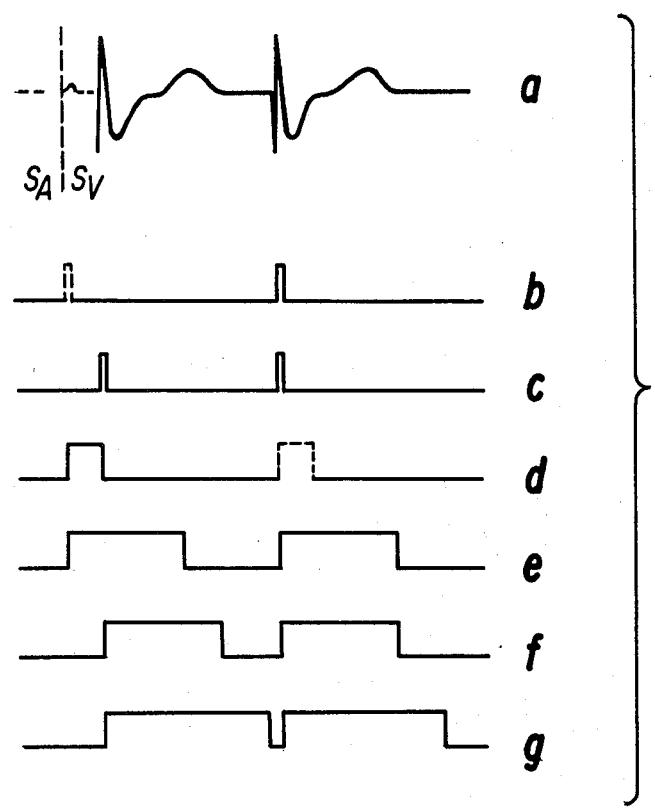

The refractory periods, as they are shown in FIGS. 6d–6g, decisively determined the possibilities of the pacemaker becoming active by way of stimulation. The pulses shown in the broken lines of FIG. 6 are not necessarily present and depend on the operating mode of the pacemaker or the prior cardiac behavior. For example, pulse $S_a$ in FIG. 6a will not appear in the inhibited mode; and the AV delay of FIG. 6d is unimportant and optional when the pacer is retrograde conducting.

Because the ventricular pulse generator 41 is never inhibited unless a partial block exists, there is no requirement in the illustrated embodiment for interference supression means. Further, there exists a significant difference between the atrial and ventricular pulse output functions. The atrial system generates pulses of the escape type by means of the timer 11. Ventricular pulses depend either on the atrial, ventricular or interference events and never occur spontaneously.

Since the simultaneous detection of a ventricular systole may occur at both electrodes of an unipolar conductor system attached to the heart, the delay member 5 generates a brief delay of a few milliseconds in order to assure that the signal being detected is evaluated correctly and is not interpretered as an event in the atrium. With the delay in the member 5, a normal P wave blocks and actuates a new cycle with a slight delay. If the first event in the cycle is a premature ventrical contraction (PVC) the short delay in the atrial processing permits the ventricular input circuit to dominate and control the behavior. In the prior art, a sequential system of this type a delay was not necessary because there was no need to distinguish premature events in unidirectional systems.

The following description of the several modes of of operation are typical for the pacemaker according to the present invention.

Figure 8:
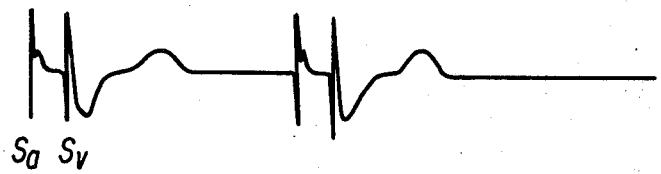

1. On the assumption that the sinus rate has a value of only 30 beats/minute (sinus bradycardia), the pacemaker generates, as shown in FIG. 8, an atrial stimulus $S_a$ followed by a ventricular stimulus $S_v$ with a given escape rate and a given time delay between the stimuli.

Figure 9:
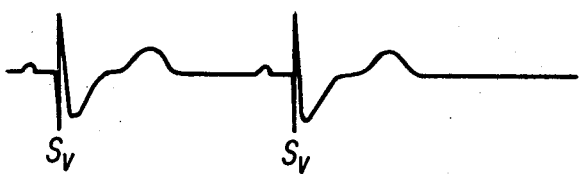

2. Referring to FIG. 9, if the sinus rate is greater than the escape rate of the pacemaker (for example 85 heartbeats/minute), the pacemaker resets its escape timer and in the illustrated mode inhibits the atrial output stimulus. The ventricular stimulus $S_v$ is delivered at the end of the given time interval independent of any requirement. This mode provides a one to one transfer and a relatively normal activity with or without physiologic transfer.

Figure 10:
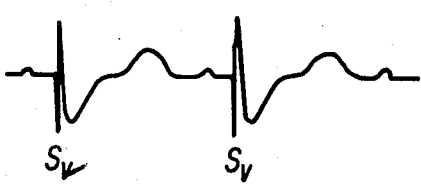

3. If the sinus rate exceeds a given value of, for example, 95 heartbeats per minute, the pacemaker generates ventricular pulses $S_v$ which appear in synchronism with the atrial signal from the heart itself but at a given shortened AV delay interval, as shown in FIG. 10. This shortening of the AV delay occurs automatically with a non-refractory, premature atrial contraction, or a fast sinus rate.

Figure 11:
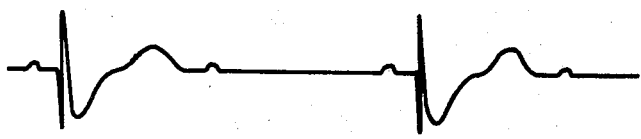

4. On the assumption that the sinus rate is higher than a given maximum value, for example, 160 beats per minute, a ventricular pulse $S_v$ is emitted in synchronism with the atrium, with shortened AV delay, and at a ratio of one for every two beats. The ventricle has a rate of 80 heartbeats per minute as shown in FIG. 11. Medically this is called a second degree block.

Figure 7:
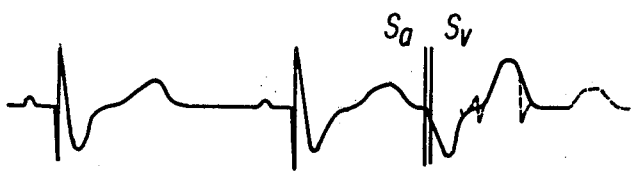
FIGS. 7–11 are diagrams illustrating the admission of stimulation pulses to the atria and ventricles independent of various intracardial signals recorded via the input stages of the pacemaker.

5. If the contraction is a premature non-refractory ventricular systole but occurs before the next atrial escape, the pacemaker emits ventricular as well as atrial pulses with a preset VA delay. In the scanning mode option this VA delay is increased with repeated consecutive occurrences in the first cycle thereafter originating from the SA node causes the system to be set back to the starting state. This sequence is illustrated to FIG. 7. This counting to provide the VA delay incrementation is provided by counter 67 of FIG. 4. If the counter is set for 8, the VA delay will be incremented 7 times before resetting to the starting VA delay, unless reset by an atrial or sinus escape.

The design of the above-mentioned component groups corresponds to that of the prior art pacemakers employing digital logic integrated circuits augmented with analog circuits (input amplifiers, output pulse amplifiers). However, the complexity and versatility of this invention may also be implemented by microcomputer class of circuits as the technology improves their reliability, lowers their current drain and improves production yield.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A cardiac pacemaker for preventing or terminating tachyarrhythmias comprising:

atrial electrode means and atrial pulse forming means for supplying stimulation pulses to the atria;

ventricular electrode means and ventricular pulse forming means for supplying stimulation pulses to the ventricle;

sensing means having an input connected to said atrial and ventricular electrode means and an output connected to said atrial and ventricular pulse forming means for detecting both atrial and ventrical systole and outputting a signal to said atrial pulse forming means in response to a detected ventricular systole to assure a coupled ventricular-atrial systole pair and outputting a signal to said ventricular pulse forming means in response to a detected atrial systole in order to assure a coupled atrial-ventricular systole pair.

2. The cardiac pacemaker of claim 1, wherein said sensing means includes amplifier means for detecting both atrial and ventricular systole and;

discriminating means for recognizing a plurality of sequences of cardiac activity and distinguishing atrial from ventricular activity.

3. The cardiac pacemaker of claims 1 or 2 further including first delay means responsive to said atrial stimulation pulses and said detected atrial systoles for delaying the output of said ventricular pulse forming means.

4. The cardiac pacemaker of claim 3 further including a second delay means responsive to a extra systole to provide an output of said atrial pulse generator.

5. The cardiac pacemaker of claim 4 further including a means for providing a refractory period following the sensing of an atrial systole.

6. The cardiac pacemaker of claim 4 further including means for providing a refractory period following the sensing of a ventricular systole.

7. The cardiac pacemaker of claim 4 further including means for providing a refractory period following the ventricular stimulus.

8. The cardiac pacemaker of claim 4 further including a means for providing a delay of the atrial sensed signal.

9. A cardiac pacemaker for preventing and terminating tachycardia comprising:

atrial pulse generating means;

atrial electrode means implantable in or near the patients' heart for receiving atrial stimulation pulses from said atrial generator means and for detecting atrial contractions;

ventricular pulse generator means;

ventricular electrode means implantable in, on or near the heart for receiving ventricular stimulation pulses from said ventricular pulse generator means and for detecting ventricular contractions;

a first time delay means connected to be actuated by signals derived from the heart behavior for supplying a stimulating pulse from said ventricular pulse generator to the ventricular electrode at a time after the occurrence of detection of an atrial contraction which ventricular stimulating pulse serves as a parallel path for the physiological atrial-ventricular transfer time;

control means for one of inhibiting and synchronizing a ventricular pulse on the detection of the occurrence of a ventricular systole; and second time delay means connected to be actuated by signals derived from the heart behavior for supplying by said atrial pulse generator means to said atrial electrode a stimulating pulse at a time after the occurrence of the detection of a ventricular contraction which atrial stimulating pulse preempts any physiologic delay path that might exist.

10. A dual sequence cardiac pacemaker for providing a atrial-ventricular stimuli pair and assuring AV sequential stimulation for all combinations of cardiac and interference signals detected on the dual electrode system comprising:

pacer escape rate determining means;

atrial stimulation means responsive to the output of said escape rate for supplying a stimulation signal to the atria;

atrial sensing means and ventricular sensing means for detecting atrial-ventricular events;

ventricular output means for supplying a stimulation signal to said ventricle;

first control means responsive to said atrial and ventricular sensing means and said atrial and ventricular stimulation signals for controlling said escape rate determining means;

second control means responsive to said atrial and ventricular sensing means and said atrial and ventricular stimulation signals to control the output of said atrial-ventricular stimulation means in a predetermined sequence in both the atrial-ventricular and ventricular-atrial direction.

11. The dual sequence cardiac pacemaker of claim 10 wherein said second control means includes a time delay means to provide a delayed ventricular stimulus along with a retrogradely provided atrial stimulation output thereby assuring atrial and ventricular sequential pacing in both directions under all conditions of cardiac activity and interference.

12. The dual sequence cardiac pacemaker of claim 10 or 11 further including a single electrode incorporating both said atrial sensing means and said ventricular sensing means.

13. The dual sequence cardiac pacemaker according to claim 12 further including an atrial sensing delay means for providing a delay of the atrial sensed signal from said atrial sensing means in order to provide electrocardiographic identification of atrial spontaneity in the presence of pacing.

* * * * *